(12) United States Patent
Ducharme

(10) Patent No.: US 8,029,509 B2
(45) Date of Patent: Oct. 4, 2011

(54) COUNTERSINK FOR USE IN ORTHOPEDIC SURGERY

(75) Inventor: Dustin Ducharme, Akron, OH (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 1250 days.

(21) Appl. No.: 11/713,190

(22) Filed: Mar. 2, 2007

(65) Prior Publication Data
US 2007/0213736 A1    Sep. 13, 2007

Related U.S. Application Data

(60) Provisional application No. 60/780,031, filed on Mar. 7, 2006.

(51) Int. Cl.
*A61B 17/00* (2006.01)

(52) U.S. Cl. .......................................... 606/80

(58) Field of Classification Search .................... 606/79, 606/80
See application file for complete search history.

(56) References Cited

U.S. PATENT DOCUMENTS 6,258,093 B1 * 7/2001 Edwards et al. ............... 606/80
7,207,995 B1 * 4/2007 Vandewalle .................. 606/104

* cited by examiner

*Primary Examiner* — Anu Ramana
(74) *Attorney, Agent, or Firm* — Hudak, Shunk & Farine Co. LPA

(57) ABSTRACT

A drill having a head that has a modified egg shape. The distal most end of the drill head is rounded and has a smaller diameter with a cutting bevel which flares into an area having a maximum diameter that is slightly larger than the diameter of the corresponding screw or implant that is used in the surgical procedure. The distal end of the drill also includes a plurality of cutting flutes which extend part of the way up the narrower portion of the drill head just up to the area having the maximum diameter. This drill can then be used to turn a countersink area into the bone at the implant site.

6 Claims, 2 Drawing Sheets

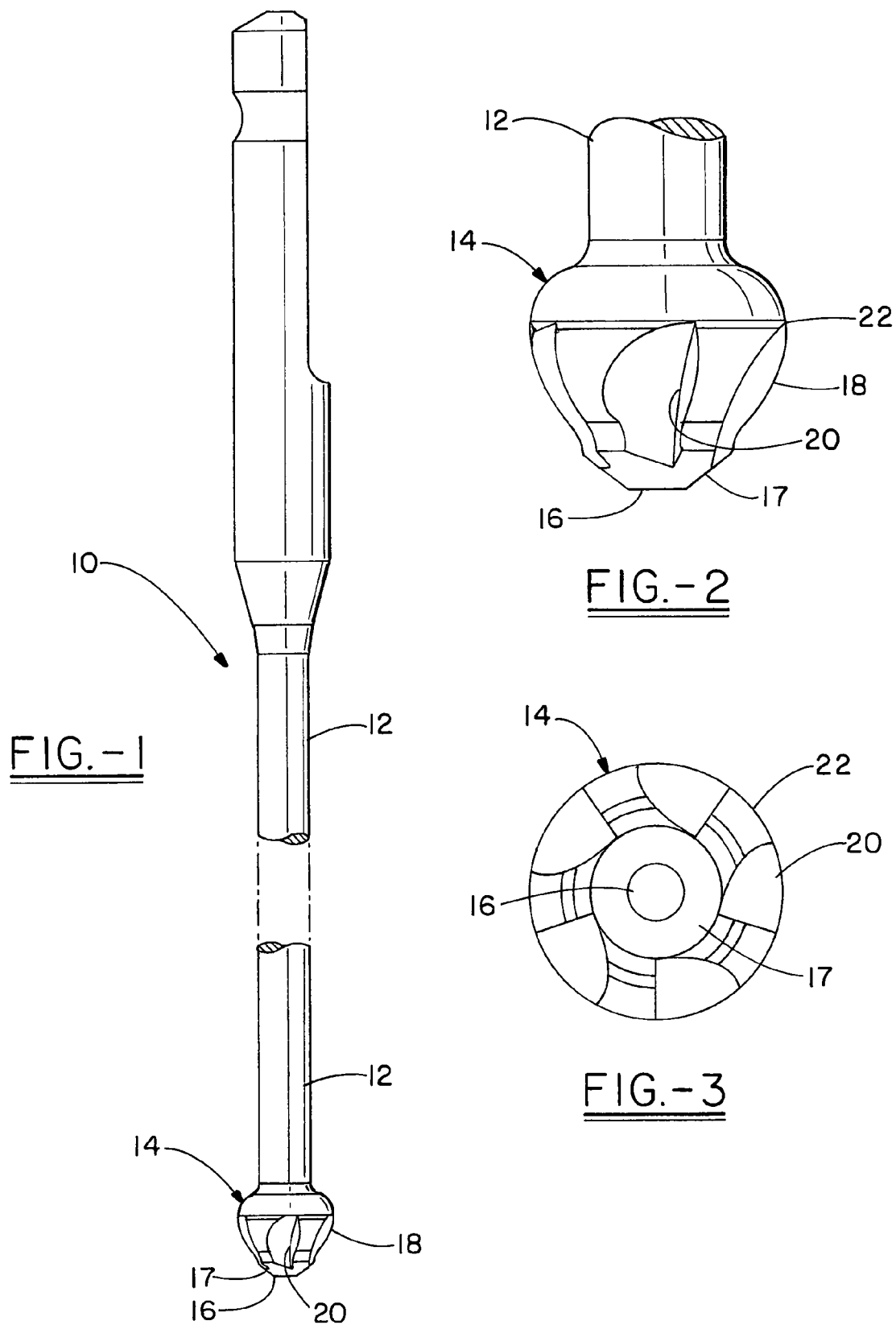

COUNTERSINK FOR USE IN ORTHOPEDIC SURGERY

This application is based on U.S. Provisional Application Ser. No. 60/780,031, filed on Mar. 7, 2006

FIELD OF THE INVENTION

The present invention relates to a drill which is adapted to impact and provide a countersink for a bone for orthopedic surgery. The drill has an egg shaped head with a plurality of cutting flutes where the profile of the head increases in diameter to an area having a diameter which corresponds to the convexly rounded shape of an orthopedic screw or peg and allows the corresponding screw or peg to be sunk flush in the cortical bone into which it is inserted.

BACKGROUND OF THE INVENTION

Some orthopedic procedures require a screw or peg to be inserted into bone in order to hold fragments together, or to hold bones in alignment to permit fusion. It is a disadvantage when the screw head projects beyond the bone surface at the insertion site. However, it is also an advantage for the screw to have a head of a sufficient size to allow sufficient torque to be applied to the screw to allow it to be easily implanted in the bone. The present invention address that issue by providing a countersink, and a drill designed specifically to provide a countersink in the cortical bone at the implantation site so that a round headed screw or peg will not remain proud or project too far beyond the surface of the bone.

SUMMARY OF THE INVENTION

The invention provides a drill having a head that has a shape like a bulb, onion dome, or a turban or a modified egg shape. In particular, the distal-most end of the drill head has a side profile is rounded and has a smaller diameter with a cutting bevel which flares into an area having a maximum diameter that is slightly larger than the diameter of the corresponding screw or implant that is used in the surgical procedure. The distal end of the drill also includes at least one, and preferably a plurality of cutting flutes, such as 2 to about 6, and preferably 5 which extend from an end portion of the drill to part of the way up the narrower portion of the drill head, and preferably just up to the area having the maximum diameter. This drill is used to turn or impact a countersink area into the bone at the implant site.

BRIEF DESCRIPTION OF THE DRAWINGS

FIG. 1 is a side view of the drill in accordance with the invention;
FIG. 2 is an enlarged side view of the cutting head of the drill of FIG. 1;
FIG. 3 is an end view of the cutting head shown in FIG. 2

DETAILED DESCRIPTION OF THE INVENTION

Figure 4:
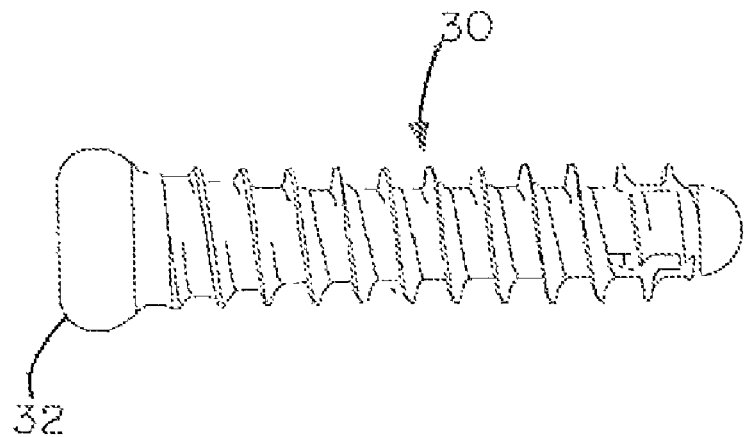
FIG. 4 is a side view of a screw to be used with the drill of FIG. 1.
Figure 5:
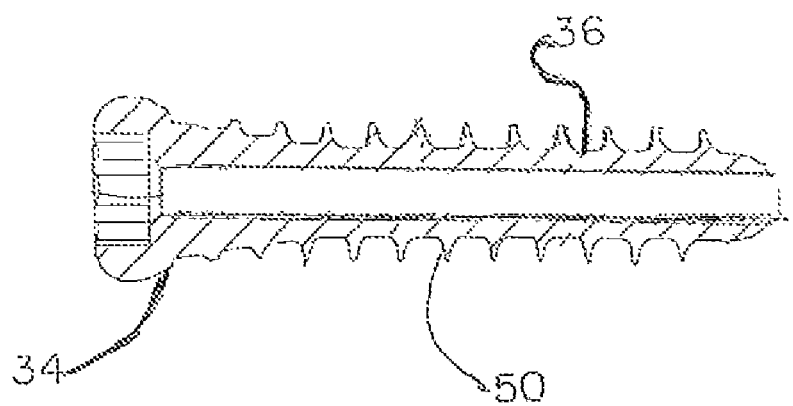
FIG. 5 is cross section of the screw of FIG. 4.

FIG. 1 illustrates a drill 10 in accordance with the invention, and which has a shaft 12 that can accommodate a handle (not shown) and a cutting head 14. The head has a complex profile with a lower cutting area 16 that includes a bevel 17 which flares into an elongated egg shaped area 18 which includes at least one and preferably a plurality of cutting flutes 20 preferably each having a cutting edge, and most preferably 3 to 5 flutes. In one embodiment, the cutting head 14 has a first diameter located on the bottom end of lower cutting area 16. The cutting head 14 diameter increases from the first diameter to a second diameter greater than the first diameter in the area of bevel 17. In a preferred embodiment, the diameter increase between the first diameter and second diameter is linear. The diameter of cutting head 14 generally increases from second diameter to maximum diameter area 22 in a non-linear fashion, and can have one or more curves, such as shown in FIG. 2 providing the cutting head 14 with a bulb-like appearance. The flutes end at the maximum diameter area 22 which is slightly larger than or corresponds to the diameter of the head of a rounded head screw 30 which is adapted to be implanted using the drill of the present invention.

The drill is used by incising and retracting the soft tissue and exposing the implantation site. An area is marked and the angle of implantation is calculated. The countersink is then formed by using the drill either manually, or with a power assist. Subsequently, a screw or peg is implanted into the site and tightened until it is flush with the bone, or at least to a point where it does not project beyond the bone so as to provide a hindrance. Preferably, the screw 30 is a cannulated screw having a proximal torque driving head 32 with a convexly rounded distal portion 34 that interfaces with the bone surface and a distal shaft 36 with an area of cancellous threads 50 adjacent a more proximal area of shaft without threads.

While in accordance with the patent statutes the best mode and preferred embodiment have been set forth, the scope of the invention is not limited thereto, but rather by the scope of the attached claims.

What is claimed is:

1. A drill and a screw system for use in orthopedic surgery wherein the screw is cannulated and has a proximal torque driving head and a distal threaded portion, the screw head having an area defining a maximum screw diameter and having a convexly rounded distal area adjacent the area defining the maximum screw diameter, and the drill comprises a shaft, a handle and a drill head, where the drill head has a modified bulb shape extending along a longitudinal axis from the distal tip to a proximal portion and the drill head is narrowest at the distal most end and has a first area of a first diameter, wherein the drill head includes from 2 to 6 cutting flutes that each define a cutting edge about the longitudinal axis and the cutting flutes flaring from about the first diameter area to at least a second area having a second diameter, and the second diameter is greater than the first diameter, and wherein a third diameter of the drill head is the maximum diameter of the drill head and the cutting edges of the cutting flutes end at the third diameter of the drill head whereby the third diameter is slightly larger than or corresponds to the maximum screw diameter which is implanted using the drill of the system.

2. The drill and the screw system as set forth in claim 1 wherein the drill head includes between 3 and 5 cutting flutes.

3. The drill and the screw system as set forth in claim 2 in which the increase in diameter between the first and the second area is a linear increase along the longitudinal axis.

4. The drill and the screw system as set forth in claim 3 wherein a third area having the third diameter is proximal to the second area.

5. The drill and the screw system as set forth in claim 4 wherein there is an increase in the diameter from the second area to the third area which is not a linear increase along the longitudinal axis.

6. The drill and the screw system as set forth in claim 5 wherein the proximal torque driving head has a convexly rounded distal portion and the shaft has a distal area of cancellous threads adjacent a more proximal area of shaft without threads.

* * * * *